United States Patent [19]

Braquet et al.

[11] Patent Number: 5,049,559
[45] Date of Patent: Sep. 17, 1991

[54] THIENO-TRIAZOLO-DIAZEPINE DERIVATIVES USEFUL AS ANTI-ISCHEMIC AGENTS

[75] Inventors: Pierre Braquet, Garches; André Esanu; Jean-Pierre Laurent, both of Paris; Jacques Pommier, Colombes, all of France

[73] Assignee: Societe de Conseils de Recherches et d'Applications Scientifiques (S.C.R.A.S.), France

[21] Appl. No.: 522,235

[22] Filed: May 11, 1990

[30] Foreign Application Priority Data

May 13, 1989 [GB] United Kingdom ................ 8911030

[51] Int. Cl.$^5$ .................... C07D 495/22; A61K 31/55
[52] U.S. Cl. ..................................... 514/219; 540/555
[58] Field of Search .......................... 540/555; 514/219

[56] References Cited

FOREIGN PATENT DOCUMENTS 254245 1/1988 European Pat. Off. ............ 540/555

OTHER PUBLICATIONS

Weber, CA 109: 1290671a (1988).

Primary Examiner—Mukund J. Shah
Assistant Examiner—Philip I. Datlow
Attorney, Agent, or Firm—Lucas & Just

[57] ABSTRACT

The invention relates to thieno-triazolo-diazepine derivatives of the formula

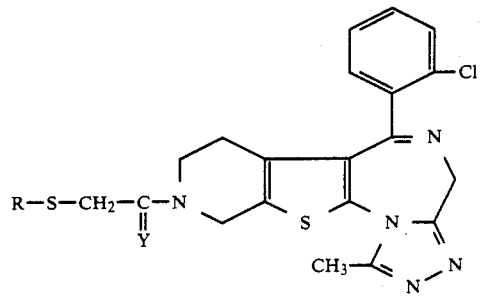

wherein Y stands for oxygen or sulphur and R stands for various substituents, to a preparation process of said compounds and to therapeutic compositions containing the same. The compounds are particularly interesting in the treatment of ischemia.

4 Claims, No Drawings

THIENO-TRIAZOLO-DIAZEPINE DERIVATIVES USEFUL AS ANTI-ISCHEMIC AGENTS

The invention relates to derivatives of thieno-triazolodiazepine which are particularly interesting as anti-ischemic, anti-asthmatic and anti-allergic agents and as gastro-intestinal protectors. The compounds of the present invention are more particularly interesting in the treatment of ischemia.

The invention provides thieno-triazolo-diazepine derivatives of the general formula A

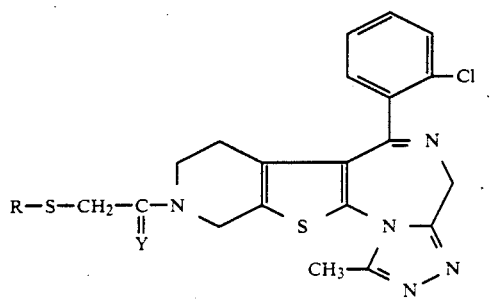

A wherein Y represents an oxygen or sulphur atom and R represents a straight chain or branched chain alkyl group having from 1 to 20 carbon atoms a phenyl group, unsubstituted or substituted by a straight chain or branched chain alkyl group having from 1 to 5 carbon atoms, an alkoxy group having from 1 to 5 carbon atoms, a halogen atom, trifluoromethyl group or an optionally substituted phenoxy group; or a furan or thiophene ring, and therapeutically acceptable salts thereof.

The invention further provides a method for the preparation of a thieno-triazolo-diazepine derivative of the general formula A, the method comprising treating the thieno-triazolo-diazepine compound of the formula B

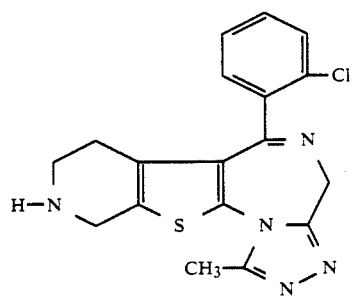

B with a compound of the formula RSCH$_2$COOH wherein R is as above defined, under nitrogen circulation, in the presence of a slight stoichiometric excess of hydroxybenzotriazole and dicyclohexylcarbodiimide, at about 0° C., and optionally treating the resulting thieno-triazolo-diazepine derivative of the general formula A wherein Y represents an oxygen atom, with Lawesson's reagent or with phosphorus pentasulphide (P$_2$S$_5$) in an aprotic solvent at a temperature of from room temperature to reflux temperature of the reacting mixture, to obtain the thieno-triazolo-diazepine derivative of the general formula A wherein Y represents a sulphur atom.

The prior art in the field of this invention, may be illustrated by U.S. Pat. No. 4 621 083 (or E.P. 176 927) in which thieno-triazolo-diazepine having PAF-antagonistic activity are disclosed.

The invention also provides a pharmaceutical composition comprising a thieno-triazolo-diazepine derivative of the general formula A as above defined in admixture with a pharmaceutically acceptable diluent or carrier.

These new compounds present a PAF-antagonistic activity from ten to a thousand times greater than this one of the diazepines disclosed in the above mentioned patent and also a more potent effectiveness.

The preparation of the starting material is described in the following preparative examples from I to X.

I—(2-chloro)benzoylmethyl cyanide

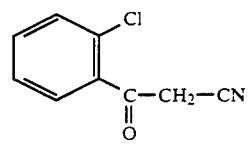

In an appropriate reactor placed under nitrogen circulation at −70° C. were poured 7 l of anhydrous THF and 115.9 g (1.36 mol) of previously dried cyanoacetic acid. Then were thus added dropwise 1 715 ml (2.74 mol) of 1,6 M solution of butyllithium in hexane, while allowing temperature to rise from −70° C. to 0° C. The reaction mixture was then stirred for one hour. Thereafter the reactional mixture was once more cooled at −70° C. and a solution of 120 g (0.685 mol) of chloro-2 benzoyle chloride in 1 l of anhydrous THF, was added dropwise.

After stirring for one hour always at −70° C., the temperature was allowed to rise from −70° C. to 0° C. for one hour. Then there was added dropwise 3 l of 1N HCl solution and after stirring for a few minutes, the reacted mixture was extracted by chloroform. The organic phase was washed with a 10% aqueous sodium bicarbonate solution, then with a saturated sodium chloride solution, dried, filtered and the solvent was evaporated off to give 135 g of residue.

The crystallization was effected by the addition of diisopropyl ether, and the product was filtered off, and washed with hexane to give 97.2 g of the title compound (Yield 79%).

II—2-amino - 3-(2-chlorobenzoyl) - 6-(ethoxycarbonyl)-4, 5,6,7-tetrahydro-pyrido [3,4 - b] thiophene.

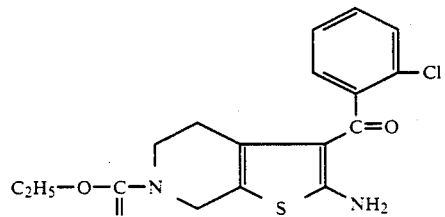

In a two liter-erlen fitted with a cooler, were poured 85.5 g (0.501 mol) of N-carbethoxy-4-piperidone, 90 g (0.501 mol) of (I), 19.3 g (0.600 mol) of flower of sulfur and 44.4 g (0.501 mol) of morpholine, in 550 ml of methanol. The mixture was refluxed for one hour. After evaporation of 250 ml of solvent, the desired compound precipitates, was filtered off, washed with ethanol, then with diethyl ether and dried to yield 155.4 g (85%) of the title compound.

III—2-(bromoacetamido) - 3-(2-chlorobenzoyl) - 6-(ethoxycarbonyl) - 4,5,6,7-tetrahydro-pyrido [3,4-b] thiophene

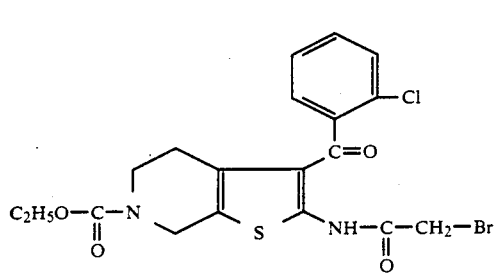

In a five liter-reactor fitted with appropriate means and with separating funnel, were poured 2.5 l of chloroform and 146 g (0.400 mol) of (II).

Then, 87.7 g (0.43 mol) of bromoacetylbromide contained in the separating funnel were added dropwise. The reaction mixture was stirred for one hour at room temperature, then washed with 300 ml of icy-water, and the organic phase was dried with anhydrous magnesium sulphate and filtered. The chloroform was evaporated off and the residue was treated with ethanol. The resulting precipitate was filtered off, washed with ethanol, then with diethyl ether, and dried to yield 184.6 g (95%) of the title compound.

IV—2-(aminoacetamido) - 3-(2-chlorobenzoyl) - 6-(ethoxycarbonyl) - 4,5,6,7-tetrahydro - pyrido [3,4 b] thiophene

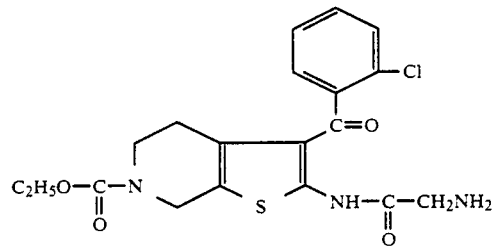

In a five liter-reactor fitted with a gas-injector were poured 174.8 g (0.36 mol) of (III) and 3 liters of THF. The suspension was cooled at 0° C. and then gaseous ammonia previously dried over potassium hydroxide was added. The addition was conducted in 8 hours. (60 g of ammonia were absorbed). The mixture was stirred overnight at 0° C., then 2 liters of THF was evaporated off under reduced pressure, and 750 ml of ethyl acetate were added.

After decantation, the organic phase was washed once with 300 ml of a 10% sodium chloride solution, three times with 300 ml of water, and dried with anhydrous magnesium sulphate. After filtration, the solvent was partially evaporated off in a rotavapor. The precipitate was allowed to stand overnight in refrigerator.

After filtration, the precipitate was washed with diethyl ether and dried to give 119 g of the title compound. The remaining organic phase was concentrated and treated with a mixture of 1.5 l of diethyl ether/THF (3/1 by volume) to give 14.6 g of the title compound (overall yield 88%).

V—5-(2-chlorophenyl) - 8-(ethoxycarbonyl) - 6,7,8,9-tetrahydro - 3H - pyrido [4',3':4,5] thieno [3,2 - f] 1,4-diazepine - 2 one

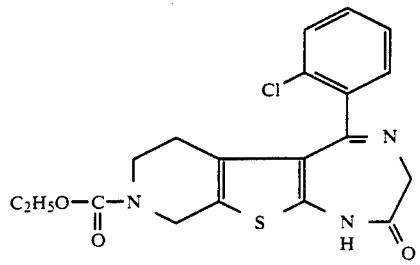

In a two liter-reactor fitted with stirring, cooling and warming means and placed under nitrogen circulation were poured 126.6 g (0.3 mol) (IV) and 800 ml of pyridine. The reaction mixture was refluxed for 18 hours.

After having checked that all the starting material had reacted, the pyridine was partially evaporated in a rotavapor under reduced pressure.

The obtained (dark brown) oil was dissolved with 1 liter of ethanol.

After cooling in an ice-bath, there was obtained a precipitate which was filtered off, washed with ethanol and diisopropyloxide to yield 101.3 g (83.6%) of the title compound.

VI—5-(2-chlorophenyl) - 8-(ethoxycarbonyl) - 6,7,8,9-tetrahydro-3H-pyrido [4',3':4,5] thieno [3,2 - f] 1,4-diazepine - 2 thione

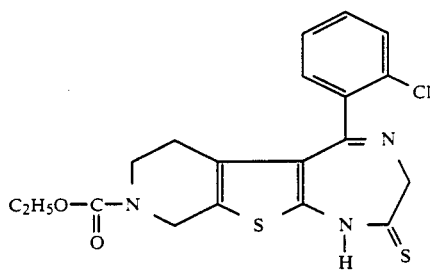

In a three liter-reactor fitted with appropriate means, were poured 93 g (0.230 mol) of V and 1,75 l of pyridine. After solubilization were added 56.3 g (0.25 mol) of phosphorus pentasulphur, and the reaction mixture was then stirred for three hours at 80°-85° C. Thereafter, the pyridine was evaporated off and the obtained residue treated with icy-water. The mixture was then extracted by methylene chloride, dried with anhydrous magnesium sulphate, filtered, evaporated and treated with diethyl-ether. Then the resulting product was filtered off, and treated with 700 ml of acetonitrile. The suspension was heated at 60° C. for 30 minutes and then allowed to cool. After filtration, and washing with acetonitrile, then with diethyl-ether, the residue was dried to yield 80.2 g (83%) of the title compound.

VII—5-(2-chlorophenyl) - 8-(ethoxycarbonyl) - 2-hydrazino 6,7,8,9 tetrahydro 3H-pyrido [4',3':4,5] thieno [3,2-f] 1,4-diazepine

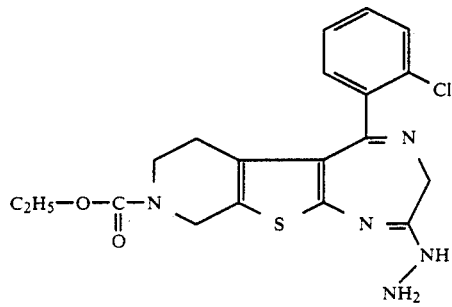

In a two liter-reactor fitted with appropriate means and with separating funnel, were poured 73.5 g (0.175 mol) of VI and 1 l of methanol. Then 26.4 ml (0.525 mol) of hydrazine hydrate contained in the separating funnel, were added at room temperature and the mixture was stirred for two hours at always room temperature.

Thereafter 1/7 of methanol were evaporated off at 30° C. and the residue was allowed to crystallize overnight in refrigerator. After filtration, washing with diethyl-ether and drying, there was obtained 65.1 g of the title compound (yield 89%).

VIII—5-(2-chlorophenyl)- 8-(ethoxycarbonyl)- 2-acetamidoamino - 6,7,8,9-tetrahydro-3H-pyrido [4',3':4,5] thieno [3,2-f]1,4-diazepine

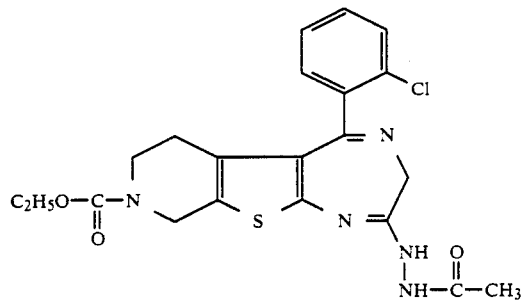

In a two liter reactor fitted with cooling means and placed under nitrogen circulation, were poured 58.5 g (0.140 mol) of VII and 1 l of tetrahydrofuran. Then 11 g (0.140 mol) of acetyl chloride and 150 ml of tetrahydrofuran were added. The addition was conducted in 30 minutes at 0° C. The solution became red after stirring for 45 minutes. The tetrahydrofuran was then evaporated off and the resulting residue treated with icy-water. Then 17.5 g of sodium bicarbonate were added and the mixture was extracted with 1 l of methylene chloride. The organic phase was washed once with water and dried with anhydrous magnesium sulphate. After filtration, the solvent was evaporated off and the resulting residue treated with diethyl-ether, filtered and dried to yield 54.1 g (84%) of the title compound.

IX—6-(2-chlorophenyl) - 9-(ethoxycarbonyl) - 7,8,9,10-tetrahydro-1-methyl-4H-pyrido [4',3':4,5] thieno [3,2-f] 1,2,4-triazolo [4,3-a] 1,4-diazepine

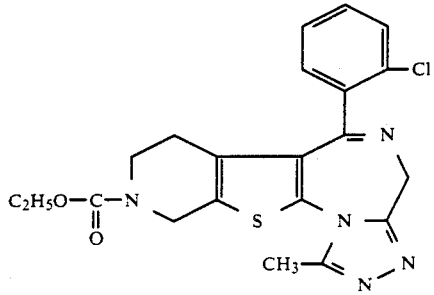

In a two liter-reactor fitted with appropriate means and placed under nitrogen circulation, were poured 750 ml of acetic acid and 46.9 g (0.102 mol) of VIII. The (red) solution was slowly warmed over one hour to reflux temperature and the reflux was thus maintained for 15 minutes. The (yellow) solution was then concentrated in a rotavapor at a bath temperature not exceeding 35° C., and the acetic acid was extracted off with 700 ml of toluene. The residue was then treated with diethyl-ether, filtered, washed with diethyl-ether, and dried to yield 42.8 g (95%) of the title compound.

X—6-(2-chlorophenyl) - 7,8,9,10-tetrahydro-1-methyl 4H-pyrido [4',3':4,5] thieno [3,2-f] 1,2,4-triazolo [4,3-a] 1,4-diazepine

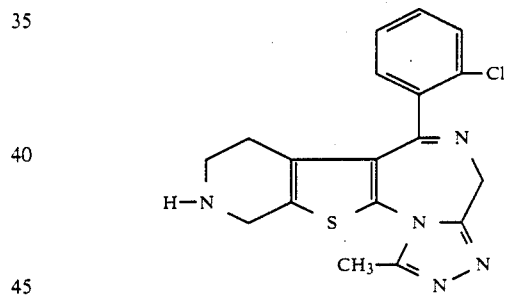

In a one liter-reactor fitted with appropriate means, were poured 500 ml of mixture of bromhydric acid/acetic acid (30% bromhydric acid by volume). Then 35.8 g (0.081 mol) of IX were added portionwise at 5° C. and the mixture was then stirred at room temperature for five days (CCM analysis showed traces of starting material). Thereafter, 250 ml of acetic acid were evaporated off and the compound precipitated. Then 250 ml of diethyl-ether were added and the mixture was stirred for 30 minutes.

The precipitate was filtered off, washed with diethyl-ether and poured into a one liter-flask in which 500 ml of icy-water were added. The pH was ajusted at pH 9.5 with addition of a 40% aqueous sodium hydroxide solution. The reaction mass temperature was maintained below 20° C. After extraction with dichloromethane, the organic phase was dried with anhydrous magnesium sulphate, filtered and the dichloromethane was partially evaporated off. Then 120 ml of ethyl acetate were added with stirring. After precipitation, 160 ml of diethyl-ether was added and the mixture was allowed to crystallize overnight in refrigerator. After filtration and washing with diethyl-ether, there was obtained 28.1 g of the title compound (yield 93,6%).

The invention is illustrated by the following examples.

EXAMPLE 1

6 -(2-chlorophenyl)- 9-(isopropylthiomethylcarbonyl)-7,8,9,10-tetrahydro-1-methyl-4H-pyrido [4',3':4,5] thieno [3,2-f] 1,2,4-triazolo [4,3-a] 1,4-diazepine Y=O R=isopropyl mp.=122°-124° C. (Tottoli) beige powder.

Into a one liter reactor fitted with stirring, cooling and warming means and placed under nitrogen circulation were poured 30 ml of dimethylformamide, 20.3 g (0.055 mol) of 6-(2-chlorophenyl)-7, 8, 9, 10 -tetrahydro-1-methyl-4H-pyrido [4',3':4,5] thieno [3,2-f] 1,2,4-triazolo [4,3-a] 1,4-diazepine and 8.9 g (0.058 mol) of isopropyl-thio-acetic acid. After cooling the mixture to 0° C., there were slowly added, under stirring, 12.36 g (0.058 mol) of dicyclohexylcarbodiimide. Stirring was maintained for 4 hours at 0° C. and then for one hour after the reaction mixture had reached room temperature. There were then added 2 g of dicyclohexylcarbodiimide and the mixture was stirred overnight.

The dimethylformamide was evacuated off by a mild warming (<60° C.) under reduced pressure. The residue was treated with 500 ml of dichloromethane, washed once with water, twice with a 10% aqueous sodium bicarbonate solution, and twice with a 10% aqueous solution of citric acid, dried over anhydrous magnesium sulphate and evaporated to dryness. The residue was then dissolved in 200 ml of ethanol and crystallized. Yield 22.2 g (83%).

EXAMPLE 2

6 -(2-chlorophenyl)- 9-(isopropylthiomethyl-thiocarbonyl)-7,8,9,10-tetrahydro-1-methyl-4H-pyrido [4',3':4,5] thieno [3,2-f] 1,2,4-triazolo [4,3-a] 1,4-diazepine Y=S R=isopropyl mp.=157°-159° C. (Tottoli) pale orange powder.

Into the same reactor as in example 1, were poured, under nitrogen circulation, 300 ml of toluene, 12.2 g (0.025 mol) of the product of example 1 and 4.75 g (0.0117 mol) of Lawesson's reagent. The reaction mixture was slowly warmed over two hours to reflux temperature and reflux was maintained for two hours. After evaporation to dryness and treatment with dichloromethane, the solution was passed on a silica gel column, eluting with dichloromethane:methanol 95:5 by volume. After evaporation to dryness of the resulting solution, the residue was recrystallized from methanol. Yield 10.2 g (82%).

The following compounds have been prepared as described in examples 1 and 2, but starting with the appropriate RSCH$_2$COOH derivative.

EXAMPLE 3

6-(2-chlorophenyl)-9-(t.butylthiomethyl-carbonyl)-7, 8, 9, 10-tetrahydro-1-methyl-4H-pyrido [4',3':4,5] thieno [3,2-f] 1,2,4-triazolo [4,3-a] 1,4-diazepine Y=O R=t.butyl mp.=169°-171° C. (Tottoli) yellow powder.

EXAMPLE 4

6-(2-chlorophenyl)-9-(t.butylthiomethyl-thiocarbonyl)- 7, 8, 9, 10-tetrahydro-1-methyl-4H-pyrido [4',3':4,5] thieno [3,2-f] 1,2,4-triazolo [4,3-a] 1,4-diazepine Y=S R=t.butyl mp.=179°-181° C. (Tottoli) pale beige powder.

EXAMPLE 5

6-(2-chlorophenyl)-9-(hexadecylthiomethyl-carbonyl)- 7, 8, 9, 10-tetrahydro-1-methyl-4H-pyrido [4',3':4,5] thieno [3,2-f] 1,2,4-triazolo [4,3-a] 1,4-diazepine Y=O R=hexadecyl mp.=292° C. (Tottoli) cream white powder.

EXAMPLE 6

6 -(2-chlorophenyl)- 9-(hexadecylthiomethyl-thiocarbonyl); 7, 8, 9, 10-tetrahydro-1-methyl-4H-pyrido [4',3':4,5] thieno [3,2-f] 1,2,4-triazolo [4,3-a] 1,4-diazepine Y=S R=hexadecyl mp.=176°-177° C. (Tottoli) white cristalline powder.

EXAMPLE 7

6-(2-chlorophenyl)- 9-(phenyl-thiomethyl-carbonyl)- 7, 8, 9, 10-tetrahydro-1-methyl-4H-pyrido [4',3':4,5] thieno [3,2-f] 1,2,4-triazolo [4,3-a] 1,4-diazepine Y=O R=phenyl mp.=243°-244° C. (Tottoli) white powder.

EXAMPLE 8

6-(2-chorophenyl)-9-(phenyl-thiomethyl-thiocarbonyl)- 7, 8, 9, 10-tetrahydro-1-methyl-4H-pyrido [4',3':4,5] thieno [3,2-f] 1,2,4-triazolo [4,3-a] 1,4-diazepine Y=S R=phenyl mp.=127°-128° C. (Tottoli) cream white powder.

EXAMPLE 9

6-(2-chlorophenyl)- 9-(4-methoxyphenylthiomethyl-carbonyl)-7, 8, 9, 10-tetrahydro-1-methyl-4H-pyrido [4',3':4,5] thieno [3,2-f] 1,2,4-triazolo [4,3-a] 1,4-diazepine Y=O R=4-methoxyphenyl mp.=180°-181° C. (Tottoli) yellow powder.

EXAMPLE 10

6-(2-chlorophenyl)-9-(4-methoxyphenylthiomethyl-thiocarbonyl)-7, 8, 9, 10-tetrahydro-1-methyl-4H-pyrido [4',3':4,5] thieno [3,2-f] 1,2,4-triazolo [4,3-a] 1,4-diazepine Y=S R=4-methoxyphenyl mp.=213°-215° C. (Tottoli) pale orange powder.

EXAMPLE 11

6- (2-chlorophenyl)- 9-(3,4-dimethoxyphenylthiomethyl-carbonyl)-7, 8, 9, 10-tetrahydro-1-methyl-4H-pyrido [4',3':4,5] thieno [3.2-f] 1,2,4-triazolo [4,3-a] 1,4-diazepine Y=O R=3,4-dimethoxyphenyl mp.=120° C. (Tottoli) pale yellow powder.

EXAMPLE 12

6-(2-chlorophenyl)-
9-(3,4-dimethoxyphenylthiomethyl-thiocarbonyl)-7, 8, 9, 10-tetrahydro-1-methyl-4H-pyrido [4',3':4,5] thieno [3,2-f] 1,2,4-triazolo [4,3-a] 1,4-diazepine Y=S R=3,4-dimethoxyphenyl mp.=130° C. (Tottoli) brown powder.

EXAMPLE 13

6-(2-chlorophenyl)-
9-(3,4,5-trimethoxyphenylthiomethylcarbonyl)-7, 8, 9, 10-tetrahydro-1-methyl-4H-pyrido [4',3':4,5] thieno [3,2-f] 1,2,4-triazolo [4,3-a] 1,4-diazepine Y=O R=3,4,5-trimethoxyphenyl. mp.=247°-249° C. (Tottoli) white powder.

EXAMPLE 14

6-(2-chlorophenyl)-9-(3,4,5-trimethoxyphenylthiomethyl-thiocarbonyl)-7, 8, 9, 10-tetrahydro-1-methyl-4H-pyrido [4',3':4,5] thieno [3,2-f] 1,2,4-triazolo [4,3-a] 1,4-diazepine Y=S R=3,4,5-trimethoxyphenyl mp.=130°-131° C. (Tottoli) beige powder.

EXAMPLE 15

6-(2-chlorophenyl)-9-(2,3,4-trimethoxyphenylthiomethyl-carbonyl)-7, 8, 9, 10-tetrahydro-1-methyl-4H-pyrido [4',3':4,5] thieno [3,2-f] 1,2,4-triazolo [4,3-a] 1,4-diazepine Y=O R=2,3,4-trimethoxyphenyl mp.=215°-220° C. (Tottoli) pale yellow powder.

EXAMPLE 16

6-(2-chlorophenyl)-
9-(2,3,4-trimethoxyphenylthiomethylthiocarbonyl)-7, 8, 9, 10-tetrahydro-1-methyl-4H-pyrido [4',3':4,5] thieno [3,2-f] 1,2,4-triazolo [4,3-a] 1,4-diazepine Y=S R=2,3,4-trimethoxyphenyl mp.=175° C. (Tottoli) orange powder.

EXAMPLE 17

6-(2-chlorophenyl)-
9-(4-t.butylphenylthiomethyl-carbonyl)-7, 8, 9, 10-tetrahydro-1-methyl-4H-pyrido [4',3':4,5] thieno [3,2-f] 1,2,4-triazolo [4,3-a] 1,4-diazepine Y=O R=4-t.butylphenyl mp.=214°-216° C. (Tottoli) yellow powder.

EXAMPLE 18

6-(2-chlorophenyl)-
9-(4-t.butylphenylthiomethyl-thiocarbonyl)-7, 8, 9, 10-tetrahydro-1-methyl-4H-pyrido [4',3':4,5] thieno [3,2-f] 1,2,4-triazolo [4,3-a] 1,4-diazepine Y=S R=4-t.butylphenyl mp.=183°-186° C. (Tottoli) pale orange powder.

EXAMPLE 19

6-(2-chlorophenyl)-
9-(2-trifluoromethylphenylthiomethylcarbonyl)-7, 8, 9, 10-tetrahydro-1-methyl-4H-pyrido [4',3':4,5] thieno [3,2-f] 1,2,4-triazolo [4,3-a] 1,4-diazepine Y=O R=2-trifluoromethylphenyl mp. 229° C. (Tottoli) pale beige powder.

EXAMPLE 20

6-(2-chlorophenyl)-
9-(2-trifluoromethylphenylthiomethylthiocarbonyl)-7, 8, 9, 10-tetrahydro-1-methyl-4H-pyrido [4',3':4,5] thieno [3,2-f] 1,2,4-triazolo [4,3-a] 1,4-diazepine Y=S R=2-trifluoromethylphenyl mp.=248°-249° C. (Tottoli) orange powder.

EXAMPLE 21

6-(2-chlorophenyl)-
9-(3-trifluoromethylphenylthiomethylcarbonyl)-7, 8, 9, 10-tetrahydro-1-methyl-4H-pyrido [4',3':4,5] thieno [3,2-f] 1,2,4-triazolo [4,3-a] 1,4-diazepine Y=O R=3-trifluoromethylphenyl mp.=311°-313° C. (Tottoli) yellow powder.

EXAMPLE 22

6-(2-chlorophenyl)-
9-(3-trifluoromethylphenylthiomethylthiocarbonyl)-7, 8, 9, 10-tetrahydro-1-methyl-4H-pyrido [4',3':4,5] thieno [3,2-f] 1,2,4-triazolo [4,3-a] 1,4-diazepine Y=S R=3-trifluoromethylphenyl mp.=177° C. (Tottoli) cream white powder.

EXAMPLE 23

6-(2-chlorophenyl)-
9-(4-trifluoromethylphenylthiomethylcarbonyl)-7, 8, 9, 10-tetrahydro-1-methyl-4H-pyrido [4',3':4,5] thieno [3,2-f] 1,2,4-triazolo [4,3-a] 1,4-diazepine Y=O R=4-trifluoromethylphenyl mp.=210°-212° C. (Tottoli) white powder.

EXAMPLE 24

6-(2-chlorophenyl)-
9-(4-trifluoromethylphenylthiomethylthiocarbonyl)-7, 8, 9, 10-tetrahydro-1-methyl-4H-pyrido [4',3':4,5] thieno [3,2-f] 1,2,4-triazolo [4,3-a] 1,4-diazepine Y=S R=4-trifluoromethylphenyl mp.=239°-241° C. (Tottoli) clear brown powder.

EXAMPLE 25

6-(2-chlorophenyl)-
9-(4-fluorophenylthiomethyl-carbonyl)-7, 8, 9, 10-tetrahydro-1-methyl-4H-pyrido [4',3':4,5] thieno [3,2-f] 1,2,4-triazolo [4,3-a] 1,4-diazepine Y=O R=4-fluorophenyl mp.=200° C. (Tottoli) pale yellow powder.

EXAMPLE 26

6-(2-chlorophenyl)-
9-(4-fluorophenylthiomethyl-thiocarbonyl)-7, 8, 9, 10-tetrahydro-1-methyl-4H-pyrido [4',3':4,5] thieno [3,2-f] 1,2,4-triazolo [4,3-a] 1,4-diazepine Y=S R=4-fluorophenyl mp.=154°-156° C. (Tottoli) white powder.

EXAMPLE 27

6-(2-chlorophenyl)-
9-(2,3-dichlorophenylthiomethyl-carbonyl)-7, 8, 9, 10-tetrahydro-1-methyl-4H-pyrido [4',3':4,5] thieno [3,2-f] 1,2,4-triazolo [4,3-a] 1,4-diazepine Y=O R=2,3-dichlorophenyl mp. 169°-170° C. (Tottoli) cream white powder.

EXAMPLE 28

6-(2-chlorophenyl)-
9-(2,3-dichlorophenylthiomethyl-thiocarbonyl)-7, 8, 9,
10-tetrahydro-1-methyl-4H-pyrido [4',3':4,5] thieno
[3,2-f] 1,2,4-triazolo [4,3-a] 1,4-diazepine Y=S R=2,3-dichlorophenyl mp.=187° C. (Tottoli) yellow powder.

EXAMPLE 29

6-(2-chlorophenyl)-
9-(4-phenoxyphenylthiomethyl-carbonyl) 7, 8, 9,
10-tetrahydro-1-methyl-4H-pyrido [4',3':4,5] thieno
[3,2-f] 1,2,4-triazolo [4,3-a] 1,4-diazepine Y=O R=4-phenoxyphenyl mp.=292° C. (Tottoli) brown powder.

EXAMPLE 30

6-(2-chlorophenyl)-9-(4-phenoxyphenylthiomethyl-thiocarbonyl)-7, 8, 9,
10-tetrahydro-1-methyl-4H-pyrido [4',3':4,5] thieno
[3,2-f] 1,2,4-triazolo [4,3-a] 1,4-diazepine Y=S R=4-phenoxyphenyl mp.=192°-195° C. (Tottoli) white cristalline powder.

EXAMPLE 31

6-(2-chlorophenyl)- 9-(2-furyl-thiomethyl-carbonyl)-7, 8, 9, 10-tetrahydro-1-methyl-4H-pyrido [4',3':4,5] thieno [3,2-f] 1,2,4-triazolo [4,3-a] 1,4-diazepine Y=O R=2-furyl mp.=121°-122° C. (Tottoli) white powder.

EXAMPLE 32

6-(2-chlorophenyl)-
9-(2-furyl-thiomethyl-thiocarbonyl)-7, 8, 9,
10-tetrahydro-1-methyl-4H-pyrido [4',3':4,5] thieno
[3,2-f] 1,2,4-triazolo [4,3-a] 1,4-diazepine Y=S R=2-furyl mp.=246° C. (Tottoli) beige powder.

EXAMPLE 33

6-(2-chlorophenyl)-
9-(2-thienyl-thiomethyl-carbonyl)-7, 8, 9,
10-tetrahydro-1-methyl-4H-pyrido [4',3':4,5] thieno
[3,2-f] 1,2,4-triazolo [4,3-a] 1,4-diazepine Y=O R=2-thienyl mp.=237°-240° C. (Tottoli) white powder.

EXAMPLE 34

6-(2-chlorophenyl)-
9-(2-thienyl-thiomethyl-thiocarbonyl)-7, 8, 9,
10-tetrahydro-1-methyl-4H-pyrido [4',3':4,5] thieno
[3,2-f] 1,2,4-triazolo [4,3-a] 1,4-diazepine Y=S R=2-thienyl mp.=198°-199° C. (Tottoli) cream white powder.

TOXICITY

The compounds of the invention are not toxic on the mice per os at the dose of 1 g/kg, by the IP or oral routes.

PHARMACOLOGY

Various pharmacological determinations have been made on these compounds; they are summarized as follows:

1) Inhibition of platelet aggregation induced by PAF

This experimentation was conducted according to the method of R. KINLOUGH. RATHBONE, J. P. CAZENAVE, M. PACKHAM and F. MUSTARD, Lab. Invest. 48, 98, 1980. In this test, New Zealand rabbits were used (male New Zealand rabbits of an average weight of 5 kg).

The determinations are made on a chrono-log Coultronics aggregometer, at 57° C. coupled with a graphic recorder; the results of these determinations (in molecular concentration) are reported on the table I on the central column.

2) Inhibition of the binding to benzodiazepine receptors

The interest of the previous experimentation depends on the results obtained in this experimentation: as a compound of the invention has a benzodiazepine like structure, it is important to check whether the specific benzodiazepine activity would not appear at the dose where platelet aggregation was inhibited.

Therefore, this experimentation has been conducted according to the method of MOHLER H. and RICHARD J. G. Agonist and antagonist benzodiazepine receptor interaction in vitro, Nature, vol. 294, 763-765, 1981.

This experimentation was conducted on rat brains incubated 1 hour 30 minutes at 4° C. using $^3$H-RO-15-1788 and $^3$H-RO-5-4864 (NEN) as tracers and RO-15-4788 and RO-5-4864 as reference antagonists.

The results in molecular concentration are reported in the table I, on the right hand column.

3) Global ischemia on gerbils

For this test, males gerbils were anaesthetized with brietal at the doses of 35 mg/kg IP; thereafter, both carotides were clamped for 10 minutes, then the clamping was released. Treated animals received each 10 mg/kg of the compounds of one of the examples.

One week later, the animals were killed and both hippocampes were taken, weighed and frozen at −80° C.

After crushing with 1 ml of TRIS-HCl pH 7.4 for 30 seconds, aliquots of each 50 μl of this preparation were incubed in each 1 ml of TRIS-HCl buffer containing $^3$H-PK 11195 at 2 nM (90 Ci/mmole, NENE, Germany) for 1 hour at 25° C.

For each preparation, 3 determinations were made. The density of omega 3 sites (marked by the specific $^3$H-PK 11195 marker) are expressed in f-moles of PK 11195/mg of fresh tissues and converted in percentage of protection compared to control.

The results of this experimentation are reported on the following table II.

PRESENTATION—POSOLOGY

In human therapy, the compounds of the invention are administered by oral route. Preferred forms of administration include tablets, gelatin capsules and the like. Usual posology is from 50 mg to 500 mg per diem according to the case. Preferred unit dose is 50 mg, associated with appropriate carriers and agents. They may be administered by injection route. Usual posology is from 5 mg to 100 mg per diem according to the case. Unit doses are from 1 to 20 mg.

TABLE I

| EXAMPLES | IC$_{50}$ | BDZ receptors |
|---|---|---|
| 1 | $2.53 \times 10^{-8}$ | $6.7 \times 10^{-6}$ |
| 2 | $2.81 \times 10^{-8}$ | $4.82 \times 10^{-5}$ |

TABLE I-continued

| EXAMPLES | IC$_{50}$ | BDZ receptors |
|---|---|---|
| 3 | $1.68 \times 10^{-8}$ | $2.3 \times 10^{-6}$ |
| 4 | $4.97 \times 10^{-7}$ | $1.55 \times 10^{-6}$ |
| 5 | $7.43 \times 10^{-9}$ | $1.21 \times 10^{-7}$ |
| 6 | $9.46 \times 10^{-9}$ | $9.1 \times 10^{-7}$ |
| 7 | $5.11 \times 10^{-7}$ | $2.1 \times 10^{-6}$ |
| 8 | $1.05 \times 10^{-8}$ | $7.33 \times 10^{-6}$ |
| 9 | $3.37 \times 10^{-8}$ | $2.7 \times 10^{-6}$ |
| 10 | $1.71 \times 10^{-8}$ | $6.6 \times 10^{-5}$ |
| 11 | $2.64 \times 10^{-8}$ | $1.4 \times 10^{-6}$ |
| 12 | $3.14 \times 10^{-8}$ | $8.7 \times 10^{-7}$ |
| 13 | $1.85 \times 10^{-8}$ | $5.5 \times 10^{-5}$ |
| 14 | $9.22 \times 10^{-9}$ | $1.5 \times 10^{-6}$ |
| 15 | $1.2 \times 10^{-7}$ | $3.6 \times 10^{-6}$ |
| 16 | $5.35 \times 10^{-8}$ | $6. \times 10^{-7}$ |
| 17 | $8.75 \times 10^{-9}$ | $4.7 \times 10^{-6}$ |
| 18 | $2.3 \times 10^{-8}$ | $4.41 \times 10^{-5}$ |
| 19 | $6.36 \times 10^{-9}$ | $2.7 \times 10^{-7}$ |
| 20 | $1.46 \times 10^{-7}$ | $1.6 \times 10^{-6}$ |
| 21 | $8.66 \times 10^{-9}$ | $8.1 \times 10^{-7}$ |
| 22 | $8.18 \times 10^{-9}$ | $6.1 \times 10^{-7}$ |
| 23 | $1.24 \times 10^{-8}$ | $1.2 \times 10^{-6}$ |
| 24 | $3.27 \times 10^{-8}$ | $3.3 \times 10^{-6}$ |
| 25 | $1.13 \times 10^{-8}$ | $6.3 \times 10^{-7}$ |
| 26 | $6.56 \times 10^{-9}$ | $6.1 \times 10^{-7}$ |
| 27 | $8.45 \times 10^{-9}$ | $4.8 \times 10^{-5}$ |
| 28 | $9.06 \times 10^{-9}$ | $4.3 \times 10^{-6}$ |
| 29 | $9.05 \times 10^{-9}$ | $1.23 \times 10^{-6}$ |
| 30 | $1.04 \times 10^{-7}$ | $3.6 \times 10^{-7}$ |
| 31 | $7.10 \times 10^{-9}$ | $2.3 \times 10^{-7}$ |
| 32 | $8.75 \times 10^{-9}$ | $1.3 \times 10^{-6}$ |
| 33 | $4.12 \times 10^{-8}$ | $5.7 \times 10^{-6}$ |
| 34 | $1.28 \times 10^{-7}$ | $7.2 \times 10^{-7}$ |

All values expressed are molecular concentration.

TABLE II

| EXAMPLES | Global protection in % |
|---|---|
| 1 | 54.2*** |
| 2 | 36.3** |
| 3 | 34.3** |
| 4 | 38.1** |
| 5 | 29.4** |
| 6 | 27.8** |
| 7 | 14.8 NS |
| 8 | 26.2* |
| 9 | 31.2** |
| 10 | 10.3 NS |
| 11 | 46.5*** |
| 12 | 34.1** |
| 13 | 32.1** |
| 14 | 19.7 NS |
| 15 | 35.8** |
| 16 | 29.3** |
| 17 | 11.1 NS |
| 18 | 12.6 NS |
| 19 | 45.6*** |
| 20 | 32.7** |
| 21 | 34.1** |
| 22 | 48.1*** |
| 23 | 37.5** |
| 24 | 38.7** |
| 25 | 14.7 NS |
| 26 | 26.5* |
| 27 | 33.3** |
| 28 | 35.3** |
| 29 | 51.6*** |
| 30 | 16.1 NS |
| 31 | 36.2** |
| 32 | 30.3** |
| 33 | 24.8* |
| 34 | 34.7** |

We claim:

1. Thieno-triazolo-diazepine derivatives of the general formula A

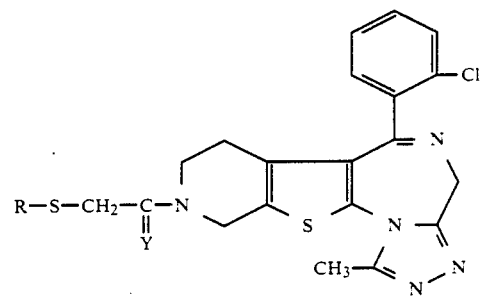

wherein Y represents an oxygen or sulphur atom and R represents a straight chain or branched chain alkyl group having from 1 to 20 carbon atoms; a phenyl group, unsubstituted or substituted by a straight chain or branched chain alkyl group having from 1 to 5 carbon atoms, an alkoxy group having from 1 to 5 carbon atoms, a halogen atom, a trifluoromethyl group or a phenoxy group; or a furan or thiophene ring, and therapeutically acceptable salts thereof.

2. A therapeutic composition of matter comprising as an active ingredient therein a sufficient amount of at least one of the compounds according to claim 1 associated with carriers suitable for the selected administration form.

3. The therapeutic composition according to claim 2, for oral administration, containing from 10 to 100 mg of active ingredient per dose unit.

4. The therapeutic composition according to claim 2, for injections, containing from 1 to 20 mg of active ingredient per dose unit.

* * * * *